United States Patent
Ho

(10) Patent No.: US 12,320,640 B2
(45) Date of Patent: Jun. 3, 2025

(54) OPTICAL SYSTEM AND INTERFERENCE OBJECTIVE MODULE THEROF

(71) Applicant: Apollo Medical Optics, Ltd., Taipei (TW)

(72) Inventor: Tuan-Shu Ho, Taipei (TW)

(73) Assignee: Apollo Medical Optics, Ltd., Taipei (TW)

( * ) Notice: Subject to any disclaimer, the term of this patent is extended or adjusted under 35 U.S.C. 154(b) by 327 days.

(21) Appl. No.: 17/762,712

(22) PCT Filed: Oct. 19, 2020

(86) PCT No.: PCT/US2020/056397
§ 371 (c)(1),
(2) Date: Mar. 22, 2022

(87) PCT Pub. No.: WO2021/077122
PCT Pub. Date: Apr. 22, 2021

(65) Prior Publication Data
US 2022/0349701 A1    Nov. 3, 2022

Related U.S. Application Data

(60) Provisional application No. 62/923,483, filed on Oct. 19, 2019.

(51) Int. Cl.
*G01B 9/02056* (2022.01)
*G01B 9/02091* (2022.01)

(52) U.S. Cl.
CPC ..... *G01B 9/02058* (2013.01); *G01B 9/02091* (2013.01)

(58) Field of Classification Search
CPC ............ G01B 9/02058; G01B 9/02057; G01B 9/0209; G01B 9/02091
See application file for complete search history.

(56) References Cited

U.S. PATENT DOCUMENTS

2004/0252310 A1* 12/2004 De Lega ............ G01B 9/02057
356/511
2006/0007557 A1* 1/2006 Davidson ............... G02B 21/02
359/656

(Continued)

FOREIGN PATENT DOCUMENTS

WO   WO 2016/126861 A1   8/2016
WO   WO 2019/056022 A1   3/2019

OTHER PUBLICATIONS

The extended European search Report in corresponding European Patent Application No. EP20877456.2, dated Sep. 18, 2023.

*Primary Examiner* — Dominic J Bologna
*Assistant Examiner* — Jonathon Cook
(74) *Attorney, Agent, or Firm* — Chang-Hsing Liang

(57) ABSTRACT

Provided herein are interference objective modules comprising an objective, and an interference module comprising a reference plate disposed apart from the objective to provide a reference arm, a beam splitter to split a source light processed from the objective, and a sample plate to translate the split light from the beam splitter to provide a sample arm, wherein the interference module is configured to make a distance of a focal plane and an interference plane of the interference objective module varied during a measurement, and wherein the focal plane and the interference plane of the interference objective module intersect during the measurement.

10 Claims, 14 Drawing Sheets

(56) References Cited

U.S. PATENT DOCUMENTS

| | | | |
|---|---|---|---|
| 2012/0099115 A1* | 4/2012 | Matsumiya | G01B 5/0014 |
| | | | 356/521 |
| 2013/0107275 A1* | 5/2013 | Boccara | G01B 9/02057 |
| | | | 356/479 |
| 2013/0242396 A1* | 9/2013 | Ishihara | G02B 21/248 |
| | | | 359/821 |
| 2016/0124202 A1* | 5/2016 | Huang | G02B 21/02 |
| | | | 359/371 |
| 2016/0209201 A1 | 7/2016 | Everett et al. | |
| 2016/0320598 A1* | 11/2016 | Dubois | A61B 90/37 |
| 2019/0265023 A1 | 8/2019 | Deck et al. | |

\* cited by examiner

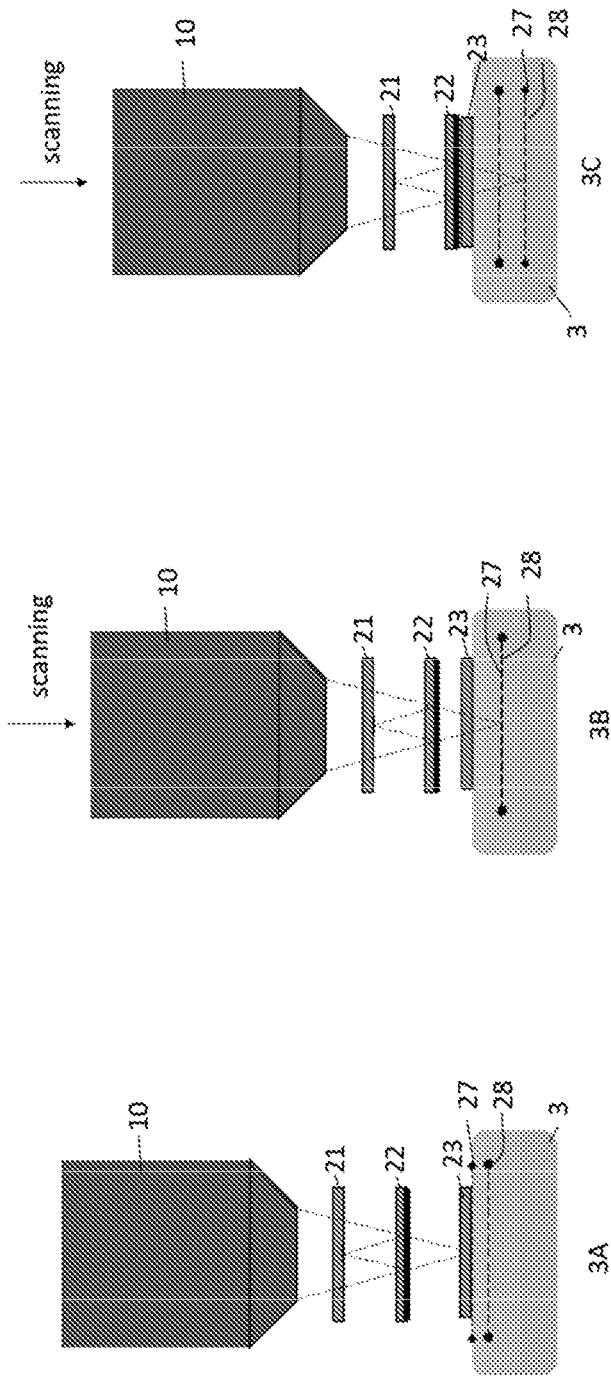
FIG. 3A-C

FIG. 7A/B
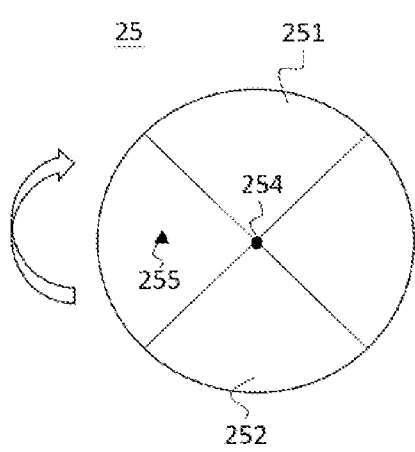
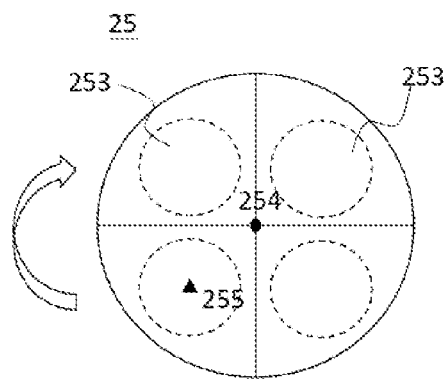
7A
7B

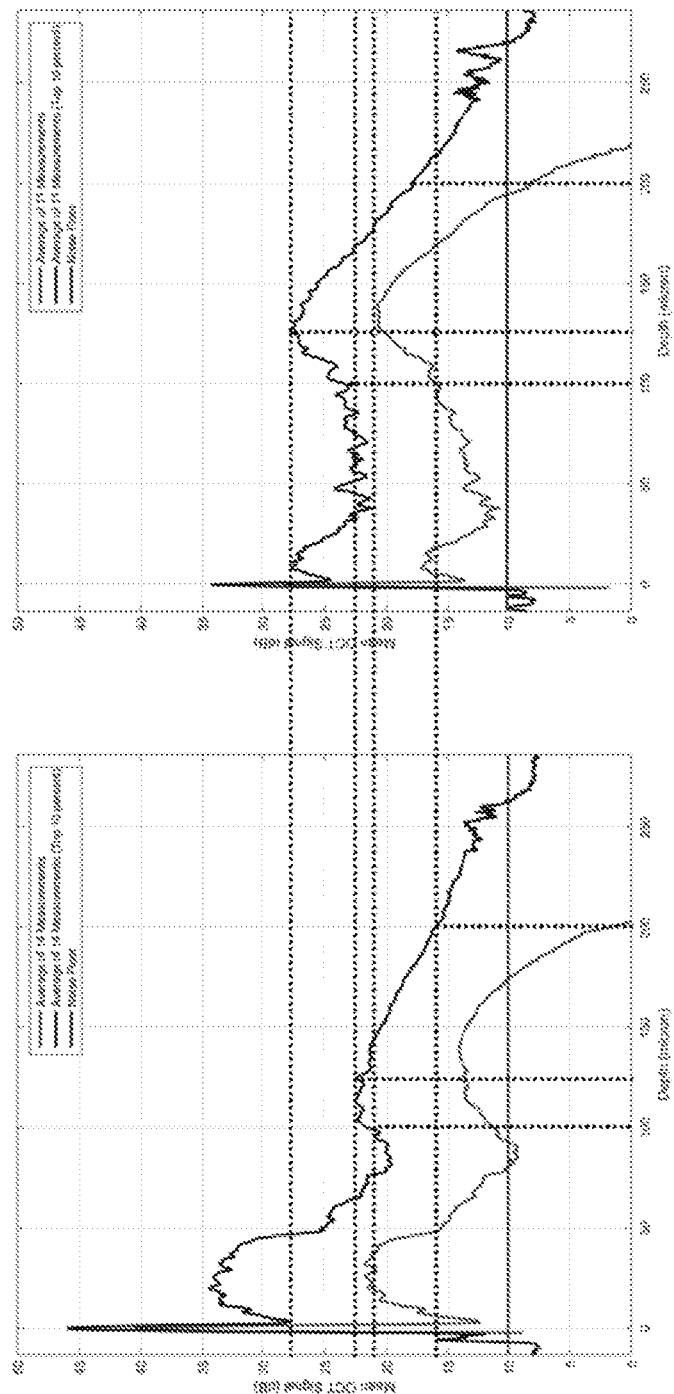
FIG. 10A/B

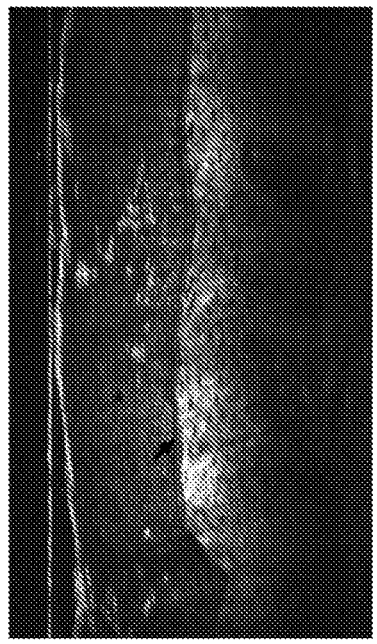
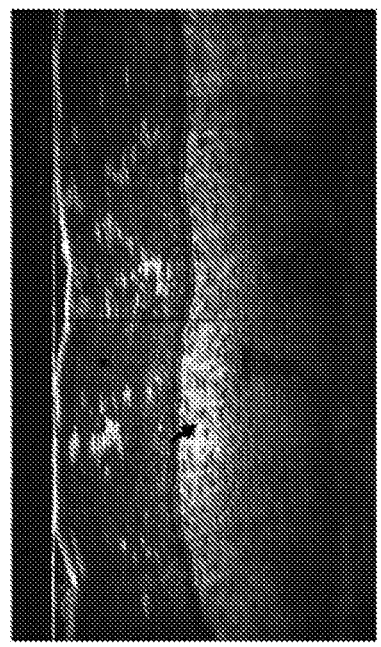
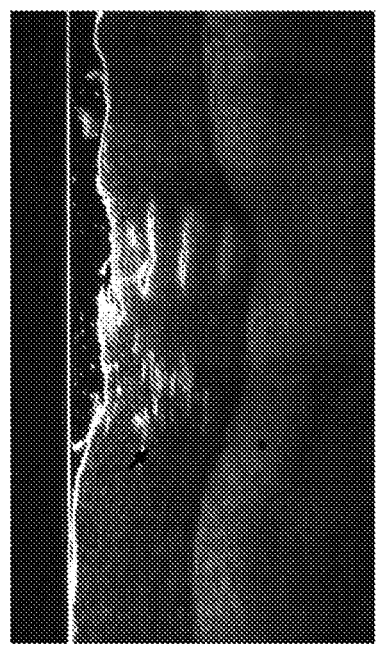
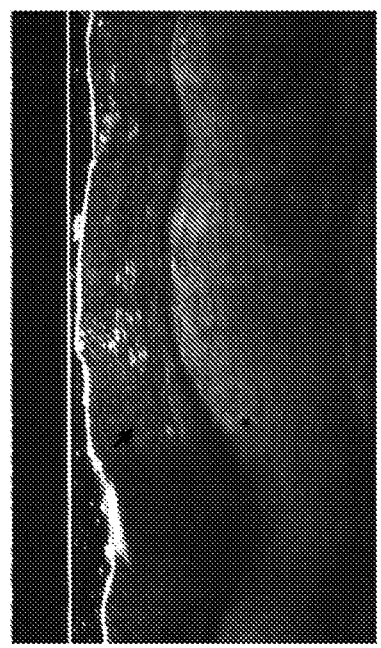
FIG. 11A-D

FIG. 12A-C
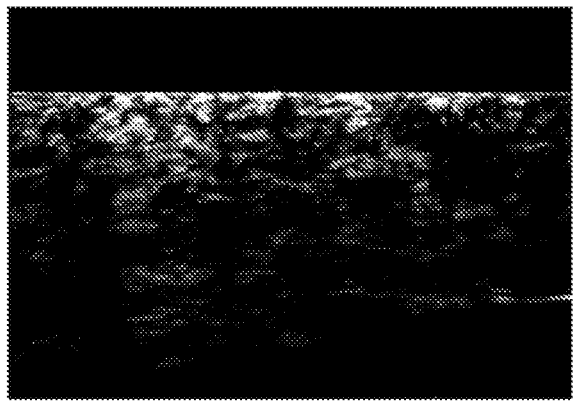
12A
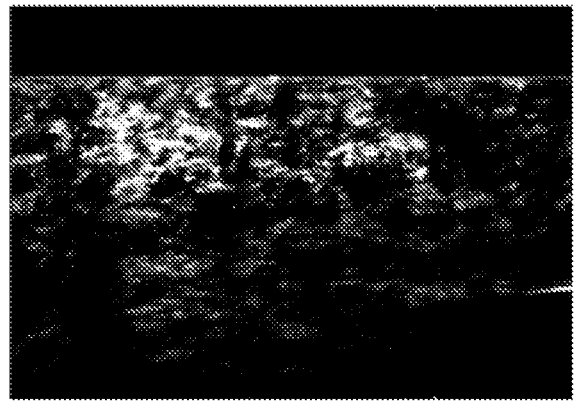
12B
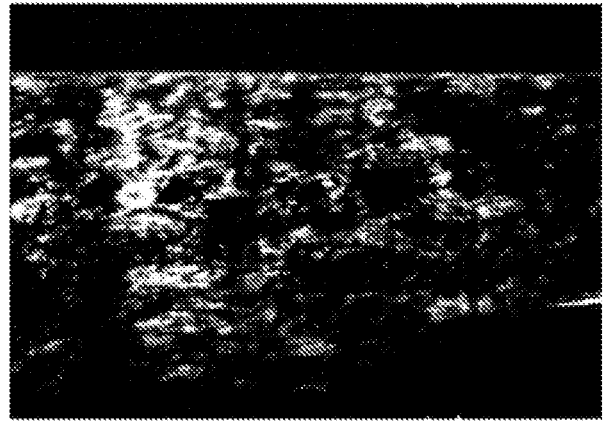
12C

OPTICAL SYSTEM AND INTERFERENCE OBJECTIVE MODULE THEROF

BACKGROUND OF THE INVENTION

Optical system is a combination of lenses, mirrors, and prisms that constitutes the optical part of an optical instrument. In recent years, the non-invasive optical system is a widely used technology, such as optical coherence tomography (OCT), reflectance confocal microscopy (RCM), two-photon luminescence microscopy (TPL), etc. There are non-invasive imaging optical systems. For example, an optical coherence tomography (OCT) system is an optical system utilizing a technique of image interferometry, that has been widely applied on imaging reconstruction of tissue. This interferometric imaging technique allows for high-resolution, cross-sectional imaging of biological samples. For imaging interferometry, broadband illumination will help the axial resolution, and high resolution cross-sectional/volumetric image can be produced.

SUMMARY OF THE INVENTION

The present invention relates to an interference objective module and the optical system thereof, which are used to improve the overall image quality of high-resolution OCT images among different tissue type.

The present invention provides an interference objective module comprising an objective, and an interference module comprising a reference plate disposed apart from the objective to provide a reference arm, a beam splitter to split a source light processed from the objective, and a sample plate to translate the split light from the beam splitter to provide a sample arm, wherein the interference module is configured to make a distance of a focal plane and an interference plane of the interference objective module varied during a measurement, and wherein the focal plane and the interference plane of the interference objective module intersect during the measurement.

In some aspect provides a device/system comprising: an illumination module configured to provide a source light to an optical interference module, which converts the source light to a line of light and processes light signal; an interference objective module disclosed herein, which handles light from the optical interference module and processes light signal generated from a sample; a two-dimensional camera configured to receive a backscattered interference signal from the sample, and a data processing module which processes the interference signal into an image.

In another aspect provides a method for imaging a sample by a device/system comprising an invention interference objective module wherein the interference module as disclosed herein is configured to make a distance of a focal plane and an interference plane of the interference objective module varied during a measurement, and making the focal plane and the interference plane of the interference objective module intersect during the measurement.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which:

FIG. 3A-C illustrate relative position of a focal plane (FP) and an interference plane (IP) of the interference objective module during a sample scanning measurement.

FIG. 7A/B illustrate examples of the refractive adjustment means as in FIG. 6.

FIG. 10A/B show exemplary SNR diagrams an exemplary optical system disclosed herein. FIG. 10A shows the result from a system comprising a Mirau interference objective module as illustrated in FIG. 6 with a glass plate as the refractive adjustment means 25. FIG. 10B shows the result of a system without the glass plate therein.

FIG. 11A-D show an exemplary cross-sectional OCT interference images produced by the optical system corresponded to FIG. 10A and FIG. 10B.

FIG. 12A-C provide interference images resulted from the optical system comprises an interference objective module as illustrated in FIG. 9.

DETAILED DESCRIPTION OF THE INVENTION

Figure 1:
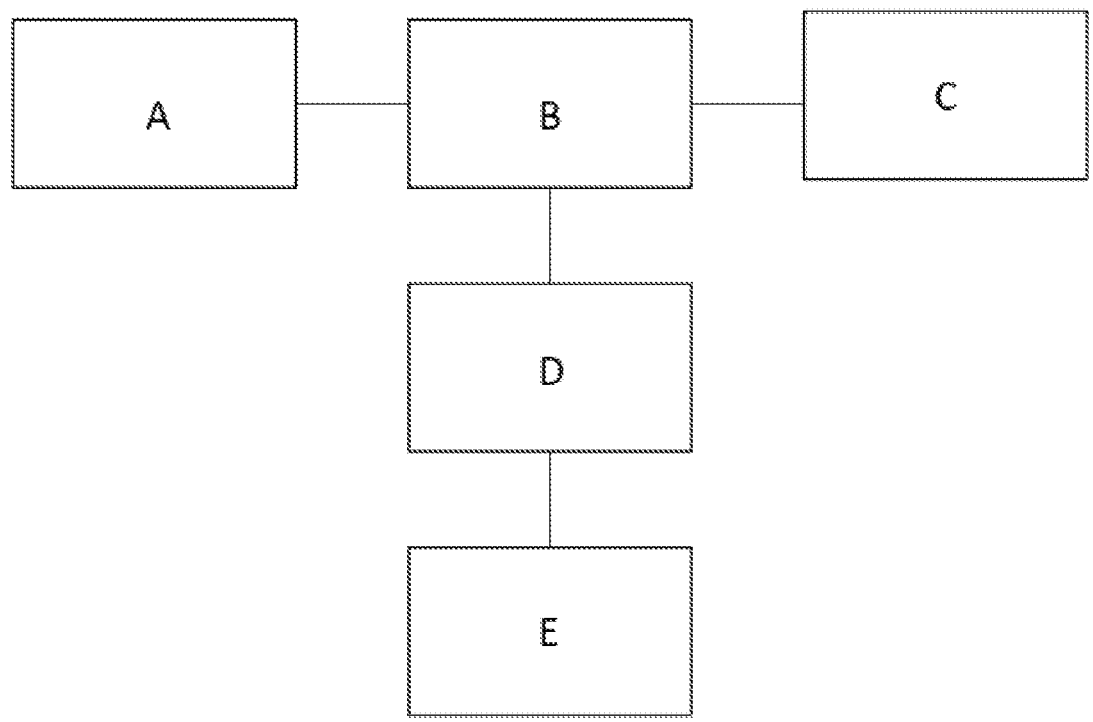
FIG. 1 illustrates a schematic diagram of the present optical system.

Optical interferometry is widely used in science and industry. It is also used in the medical filed such as dermatology, ophthalmology, or oral health. In the field of medical application, the refractive index is not always homogeneous in the whole tissue. For instance, the refractive index of stratum corneum and cancerous tissue is usually higher than other skin tissue. Therefore, it is not easy to observe features with cellular resolution in the whole tissue. The present invention provides an optical system with specific interference objective module to improve the above defects while maintaining high resolution and SNR value to adjustably observe different depth of sample.

Combining high-numerical-aperture optics and broadband light source, near-isotropic spatial resolution around one micron can be achieved by OCT. This feature makes OCT an efficient tool to provide cellular resolution imaging. One of the problems of the system is the limited depth of focus (DOF). For the limited DOF, a small portion of the OCT cross sectional (B-scan) images will have a good resolution, but most are blurred. There are some methods to resolve this problem including image fusion, Bessel beam generation, dynamic focusing, etc. Most of the methods require some compromise in spatial resolution (i.e. image fusion) or sensitivity (i.e. Bessel beam). One method that optimize the spatial resolution and sensitivity is to translate the focal plane and interference plane simultaneously during axial scanning; however, there are two problems of this approach. First, since the optical properties of sample (i.e. refractive index) are usually unknown a priori and varies greatly between tissues, it is difficult to maintain the same imaging performance among different tissues. This problem is severe in system with high numerical aperture, where DOF is narrow and the system is sensitive to variance of sample properties. The other problem is that at least two axial scanning modules are necessary in order to translate both focal plane and interference plane without moving the sample (i.e. the patient), and the system cost and complexity would be significantly increased.

One of the problems of high-resolution OCT imaging within biological tissue is the mismatch between focal plane (FP) and interference plane (IP). For OCT with dynamic focusing (focal plane (FP) translating during axial scanning), in principle, this problem can be avoided by carefully choosing immersion liquid with refractive index (RI) similar to the sample tissue. But the refractive index (RI) of biological tissues is always depth-dependent and varies among different body sites, so it is difficult to avoid the mismatch between focal plane (FP) and interference plane (IP). In some circumstances, this problem will degrade the spatial resolution of the image. For OCT based on low-spatial-coherence light sources (i.e. halogen lamp), since the out-of-focus signals can hardly interfere, this also cause severe sensitivity degradation than system with spatially-coherent light sources (i.e. supercontinuum sources).

Methods proposed to resolve this problem includes using numerical methods for image refocusing, or by using particular scanning elements (e.g., objective lens and reference module) to compensate this mismatch. The current invention provides a system/method to minimize the mismatch between focal plane (FP) and interference plane (IP) by selecting immersion liquids with refractive index (RI) either slightly larger or smaller than the sample tissue, and/or introducing a built-in mismatch with reverse sign and to the interferometer. With this setup, the system can cover a larger variety of tissue type, and it can be extended by changing the amount of build-in mismatch.

A simple model of the mismatch between focal plane (FP) and interference plane (IP) is described as followed. First, define the depth scan velocity of the focal plane (FP) is $v_{FP}$ and the depth scan velocity of the interference plane (IP) is $v_{IP}$. If the scanning velocities are constant during the scanning, then the mismatch can be expressed as:

$$\Delta z = \frac{(v_{FP} - v_{IP})}{v_{IP}} z + \Delta z_0 = \beta z + \Delta z_0$$

The $\Delta z$ is the mismatch between focal plane (FP) and interference plane (IP), z is the depth position of the interference plane (IP), $\Delta z_0$ is the above-mentioned build-in mismatch, and $\beta$ is increment rate of mismatch to the depth. In this simple model (constant velocity of each plane), the minimum overall mismatch can be achieved in case both $\beta$ and $\Delta z_0$ are zero, and they shall be of opposite sign if $\beta$ and/or $\Delta z_0$ are non-zero.

For OCT with only one scanning axis (i.e. Michelson/Linnik interferometer with related motion between interferometer and sample, or Mirau-type interferometer), the moving speed of each plane within the sample (related to last surface of the interferometer or the superficial surface of the sample) can be estimated as:

$$v_{IP} = \frac{n_O}{n_{sam}} v_O$$

$$v_{FP} = \frac{n_{sam}}{n_O} v_O$$

The $v_O$ is the relative velocity between the interferometer and the sample, $n_O$ is the refractive index of spacing (usually filled by immersion liquid) between them, and $n_{sam}$ is the refractive index of the sample. For in vivo tissue imaging, it is common that the average refractive index of the sample varies with depth. More precisely, the upper layers may have either higher or lower refractive index than the lower layers. For example, the superficial skin is composed of stratum corneum and epidermis, and the averaged refractive index of stratum corneum is generally higher than epidermis. Since the $n_{sam}$ is depth-dependent, the $v_{IP}$ and $v_{FP}$ are also a function of depth, even with a constant $v_O$.

An example for the consideration of choosing $n_O$ (i.e. refractive index of immersion liquid) and $\Delta z_0$ (amount of build-in mismatch) is provided below. If $n_{sam}$ decreases with depth, so is the $\beta$. In this case, the initial value of $\beta$ is preferred to be positive, so the overall absolute value of can be minimized, therefore $n_0$ shall be chosen to be less than the $n_{sam}$ of the superficial region of the sample. And in this case, the value of $\Delta z_0$ shall be negative to minimize the overall $\Delta z$.

In order to solve the above mentioned problem, the present invention provides an embodiment of an optical system as FIG. 1, which comprises a light source A providing a source light to an optical interference module B; an interference objective module C, which handles light from the optical interference module B and process light signal generated from a sample; and a detector D, which detects an interference signal from the sample. In addition, a data processing module E can be disposed to process the interference signal into an interference image.

Figure 2A:
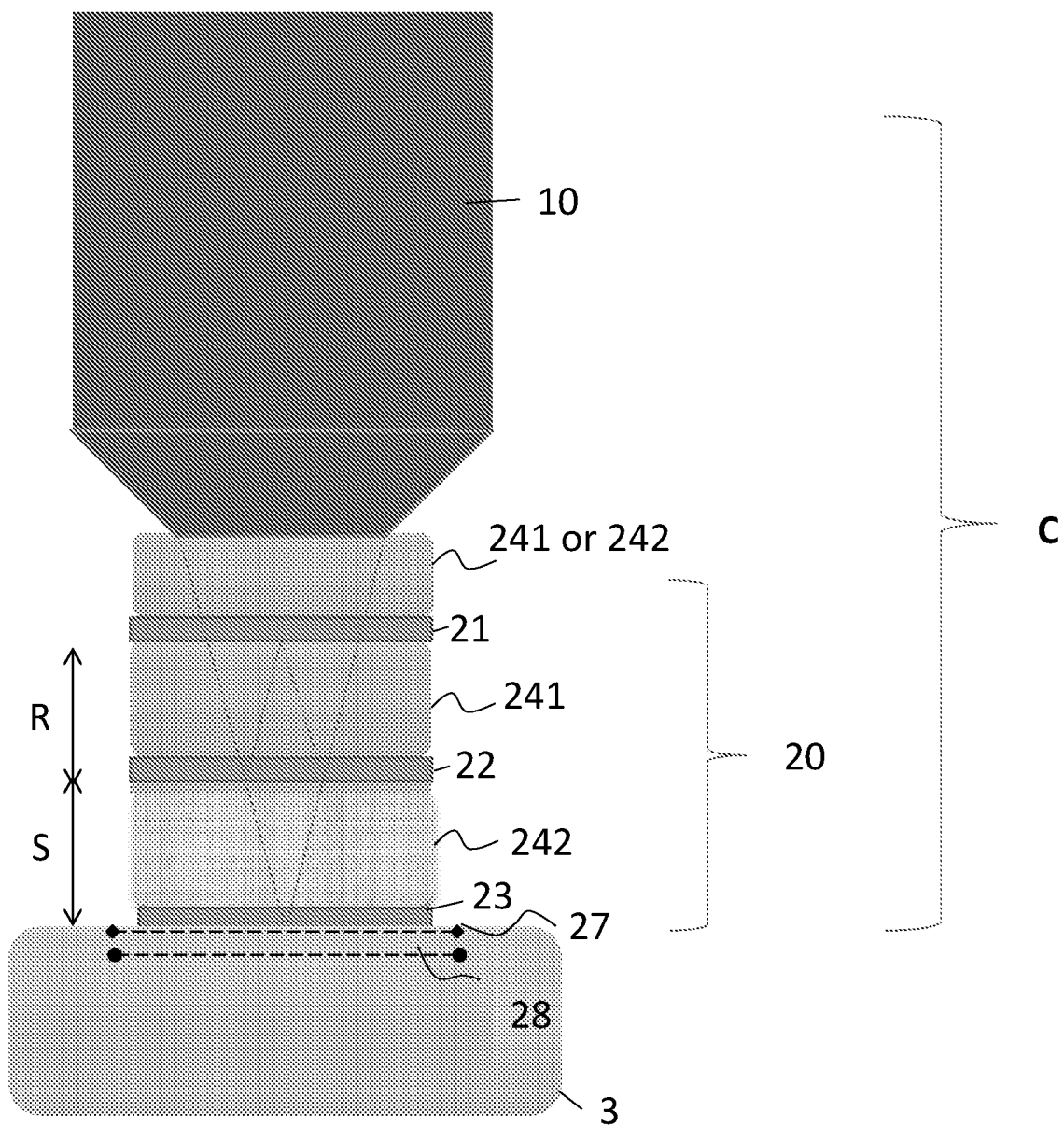
FIG. 2A illustrates an embodiment of a Mirau interference objective module of the present invention.

The interference objective module C comprises an objective and an interference module. The interference module comprises a beam splitter for separating the source light; a reference plate for providing a reference arm; and a sample plate for processing a sample arm from the sample. FIG. 2A illustrates an exemplary Mirau type interference objective module. The Mirau interference objective module comprises an objective 10 and an interference module 20, wherein the interference module 20 includes a reference plate 21 disposed apart from the objective 10 to provide a reference arm; a beam splitter 22 used to split source light processed from the objective 10 and the reference plate 21; and a sample plate 23 disposed to translate the split light from the beam splitter 22 and process the back scattered light from the sample 30. In some embodiments, the reference plate, beam splitter and sample plate each independently is in a form of glass such as a fused silica with refractive index and thickness in a manner of less dependent to temperature variation.

The interference module 20 is configured to make a distance of a focal plane 27 and an interference plane 28 of the interference objective module C varied during a measurement. The focal plane 27 and the interference plane 28 of the interference objective module C are overlapped on a certain position during the measurement, and the certain position is usually a certain depth within a sample (i.e., the focal plane and the interference plane of the interference objective module intersect during the measurement).

Herein, FIG. 3A-C illustrate relative positions of the focal plane (FP) 27 and the interference plane (IP) 28 of Mirau type interference objective module during a measurement process. Before starting the measurement, the focal plane (FP) 27 is locate on the interface of sample plate 23 and sample 30, and the interference plane (IP) 28 is located inside sample 30 without overlapped with the focal plane (FP) 27 (FIG. 3A). When the objective scanning toward the sample 30, distance between the focal plane (FP) 27 and the interference plane (IP) 28 gets close to each other, then overlap in a certain depth within the sample 3 (FIG. 3B). Usually, the overlapped position has the clearest image quality during the scanning measurement. While continuously scanning deep into the sample 3, the focal plane (FP) 27 and the interference plane (IP) 28 will be apart from each other (FIG. 3C). Accordingly, the distance between the focal plane (FP) 27 and the interference plane (IP) 28 is varied during the process of sample scanning.

Non overlapping of focal plane (FP) and interference plane (IP) of the interference objective module are achieved due to asymmetry of sample arm and reference arm. In order to achieve that asymmetry property, in certain embodiments, Mirau type interference objective module comprises at least two different media filled in the interference module 20.

In order to receive better interference imaging quality, in some embodiments, a Mirau type interference objective module as illustrated in FIG. 2A is filled with at least two different media with a refractive index similar to the sample of measurement. The first media 241 and the second media 242 are filled in spaces inside the Mirau type interference objective module. In some embodiments, the first media or the second media is filled in a space between the objective 10 and the reference plate 21. In some embodiments, the first media is filled in a space between the reference plate 21 and the beam splitter 22. The at least two different media have a refractive index similar to sample 3 in a range of about 1.2 to about 1.8. In some embodiments, the first media has a refractive index in a range of about 1.3 to about 1.5. In some embodiments, the first media comprises water, silicone oil, silicone gel, ultrasonic gel, ethanol or glycerol with a refractive index in a range of about 1.3 to about 1.5, or combinations thereof. In certain embodiments, the first media comprises water, silicone oil, or glycerol. In certain embodiments, the first media comprises silicon oil. In some embodiments, a second media 242, different from the first media, is filled in a space between the beam splitter 22 and the sample plate 23. In some embodiments, the second media has a refractive index different from the refractive index of the first media 241, but still in a range of about 1.2 to about 1.8. In certain embodiments, the second media comprises a silicone gel such as ST-Elastomer 10, or its counterpart elastomers, or the like.

In certain embodiments, when the refractive index of the sample 3 is larger than a refractive index of skin, equations (1) to (3) will be satisfied:

$$n_{average\ sample} < n_{average\ reference} \quad (1)$$

$$d_{sample} > d_{reference} \quad (2)$$

$$n_{average\ sample} \times d_{sample} = n_{average\ reference} \times d_{reference} \quad (3)$$

According to FIG. 2, "$n_{average\ sample}$" represents an average refractive index of the Zone S, which means the average refractive index of sample arm and it is defined as $$n\ average\ sample = \frac{1}{d\ sample}\sum n j d j,$$

n represents refractive index of each material sample arm passing through in Zone S, and d represents thickness of that each material. "$n_{average\ reference}$" represents an average refractive index of Zone R, which means an average refractive index of reference arm and it is defined as $$n\ average\ reference = \frac{1}{d\ sample}\sum n i d i,$$

n represents refractive index of each material reference arm passing through in Zone S, d represents thickness of that each material. "$d_{sample}$" represents a distance of Zone S, and "$d_{reference}$" represents an average refractive index of Zone R.

In some embodiments, when the refractive index of the sample 3 is smaller than a refractive index of skin, equations (4), (5) and (3) will be satisfied.

$$n_{average\ sample} > n_{average\ reference} \quad (4)$$

$$d_{sample} < d_{reference} \quad (5)$$

$$n_{average\ sample} \times d_{sample} = n_{average\ reference} \times d_{reference} \quad (3)$$

Symbols in equations (4), (5), and (3) are defined the same as equations (1), (2), and (3).

In some embodiments, to achieve an asymmetry of sample arm and reference arm, the thickness and/or material of the sample plate 23 is different from the beam splitter 22.

In certain embodiments, the thickness and/or material of the sample plate 23 is modified/chosen to satisfy equations (1) to (5). In certain embodiments, the thickness and/or the material of the sample plate 23 is different from the beam splitter 22 (and optionally the reference plate 21). In some embodiments, thickness and/or material of the beam splitter 22 is modified/chosen to satisfy equations (1) to (5). In certain embodiments, the thickness and/or the material of the beam splitter 22 is different from the sample plate 23 (and optionally the reference plate 21). In some embodiments, the material difference is characterized by a refractive index.

Figure 2B:
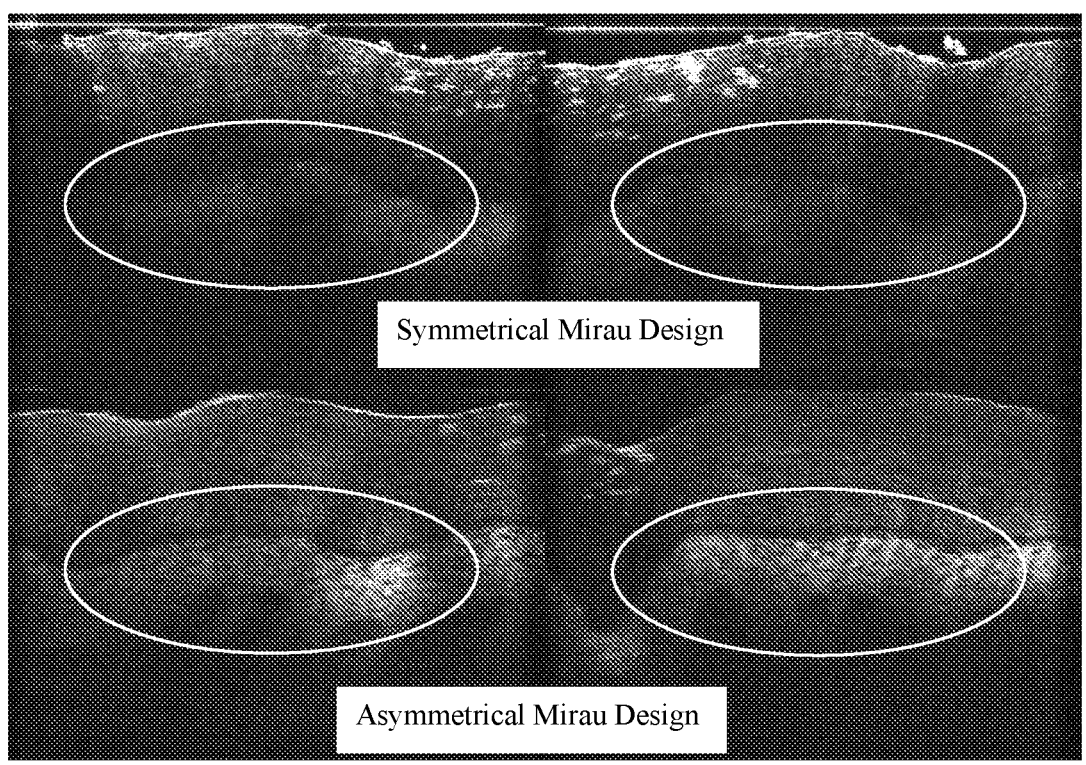
FIG. 2B provides exemplary interference images produced by the optical system in accordance with the design of FIG. 2A wherein top images are produced by the symmetrical design and the bottom images are produced by the asymmetrical design.

FIG. 2B provides exemplary interference images produced by the optical system in accordance with the design of FIG. 2A, whereas top images are produced by the symmetrical design where the same media was used to fill in the module 20 with the same thickness of the beam splitter 22 and the reference plate 23. The better bottom images are produced by the asymmetrical design where two different media were used to fill in the interference objective module 20 with the same thickness of the beam splitter 22 and the reference plate 23. All the B-scan images are acquired at human palm. The B-scan images acquired with asymmetric design show better sensitivity and resolution at epidermis.

Figure 2C:
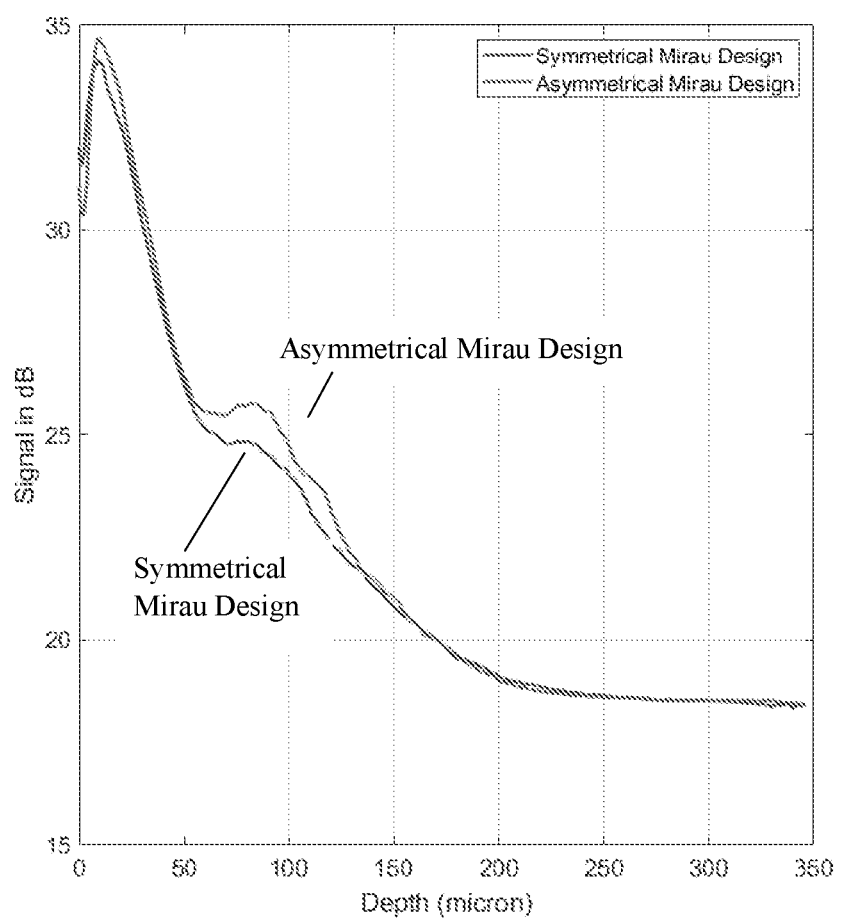
FIG. 2C provides a SNR diagram produced by the optical system in accordance with the design of FIG. 2A wherein top line is produced by the asymmetrical design and the bottom line is produced by the symmetrical design.

FIG. 2C provides a SNR diagram of an exemplary optical system comprising a Mirau interference objective module as illustrated in FIG. 2A. The top line is resulted from the asymmetric design where two different media were used to fill in the interference objective module and two different thicknesses of the beam splitter 22 and the reference plate 23 were used. The bottom line is resulted from the symmetrical design with same media used to fill in the interference objective module 20 with the same thickness of the beam splitter 22 and the reference plate 23. The signal to noise (SNR) profile versus depth is estimated by average of >15 B-scans of human skin. By changing the conventional symmetrical Mirau design to one asymmetrical Mirau design with different media and different glass thickness, the overall SNR is improved.

With an exemplary Mirau interferometry disclosed herein, the simultaneous translation of the focal plane (FP) and interference plane (IP) can be achieved by simply moving the Mirau objective lens. The Mirau-type OCT also has a higher resistance to vibration, requires less optical elements and is more compact comparing to Michelson and Linnik interferometry. One of the problems of Mirau structure is it has less degree of adjustability. Since the reference arm and sample arm share the same objective lens in Mirau interferometry, it is difficult to add an additional scanning axis (such as a second axis) for mismatch compensation. Since the present invention can selectively use second axis to compensate the mismatch, it is useful for Mirau-type OCT.

Figure 4:
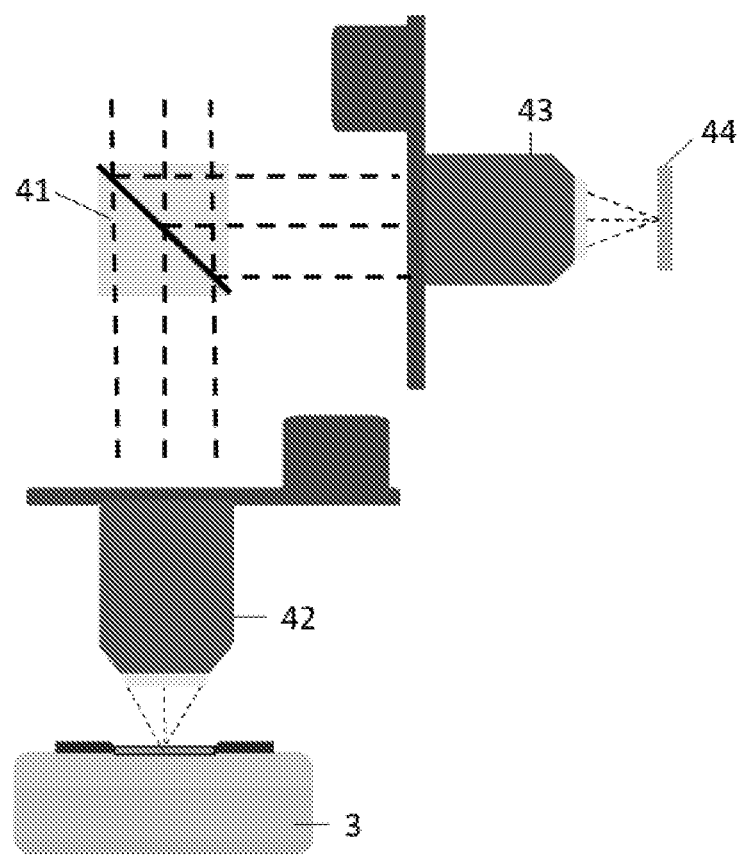
FIG. 4 illustrates an embodiment of an exemplary Lynnik type interference objective module of the present invention.

The interference objective module C is not limited in Mirau type, but can be a Michelson type, a Linnik type, or a Mach Zender type. FIG. 4 provides a Lynnic type interference objective module as an example, which comprises a beam splitter 41 for splitting source light to a reference objective 43 and a sample objective 42. The reference objective 43 projects the split light to a reference mirror 44 to produce reference arm, and the reference arm interferes with the sample arm back scattered from the sample 3. The reference objective 43 and the sample objective 42 will be separately adjusted during a measuring process.

Figure 5:
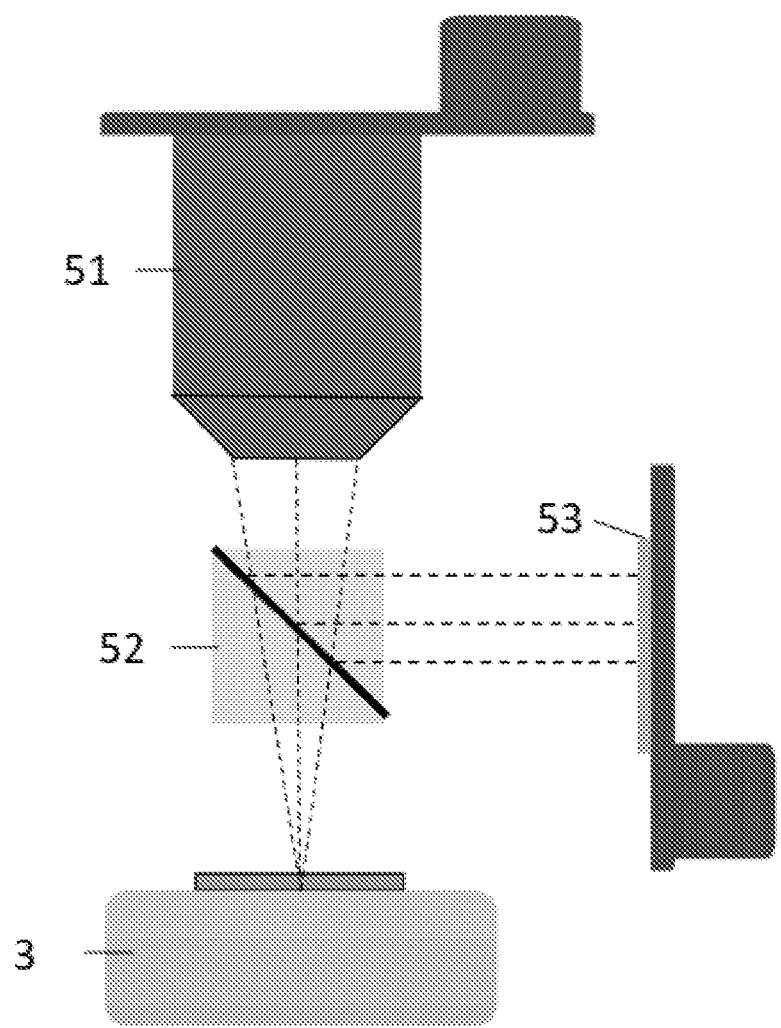
FIG. 5 illustrates an embodiment of an exemplary Michelson type interference module of the present invention.

A Michelson type interference objective interference module is provided as an example in FIG. 5, which comprises an objective 51 to process source light to a beam splitter 52, then the split light will be projected on the sample 3 and the reference mirror 53. Then the reference arm and the sample arm from the reference mirror 53 and the sample 3 interferes to produce interference signals. The objective 51 and the reference mirror 53 can be adjusted during a measuring process.

Figure 6:
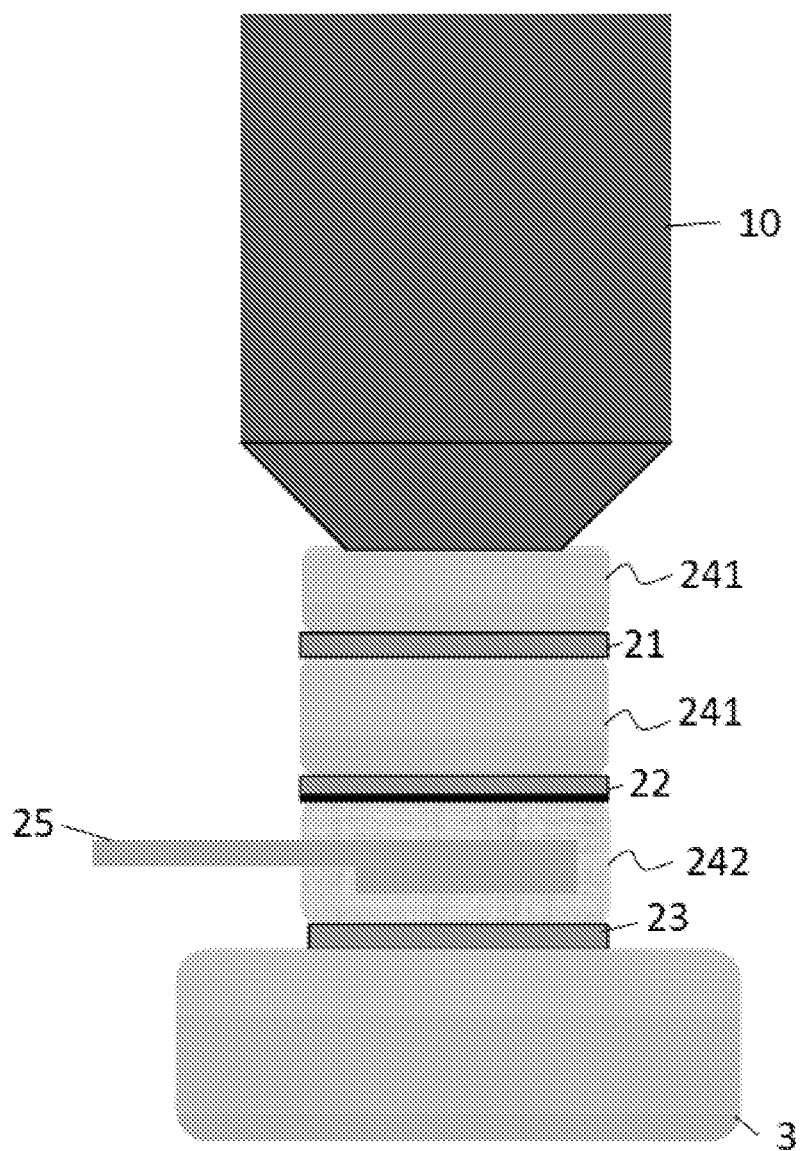
FIG. 6 illustrates an embodiment of an exemplary Mirau type interference module with a refractive adjustment means.

In order to adjust the overlapping position of the focal plane and interference plane, in some embodiments, a refractive adjustment means 25 is disposed between the beam splitter 22 and the sample plate 23 of a Mirau type interference objective module as illustrated in FIG. 6. The first media 241 and the second media 242 are filled in spaces inside the Mirau type interference objective module. In some embodiments, the refractive adjustment means 25 comprises a glass plate, a rotational plate, or the like. In some embodiments, the refractive adjustment means 25 is a rotational plate including a plurality portions with different thickness and/or refractive index as shown in FIG. 7. The refractive adjustment means 25 (i.e., a rotational plate) can be divided into several parts comprising a thick glass plate 251 part and a thin glass plate 252 part (FIG. 7A), wherein the rotational axis 254 is located on the central of the refractive adjustment means 25 (i.e., a rotational plate), and the optical axis 255 is located on the portion of the glass plates 251, and 252. In certain embodiments, the refractive adjustment means 25 can be designed as shown in FIG. 7B with multiple glass patch 253 in a different thickness or refractive index fused on the refractive adjustment means 25. The optical characterization of each portion on the refractive adjustment means 25 can be varied as demand.

Figure 8:
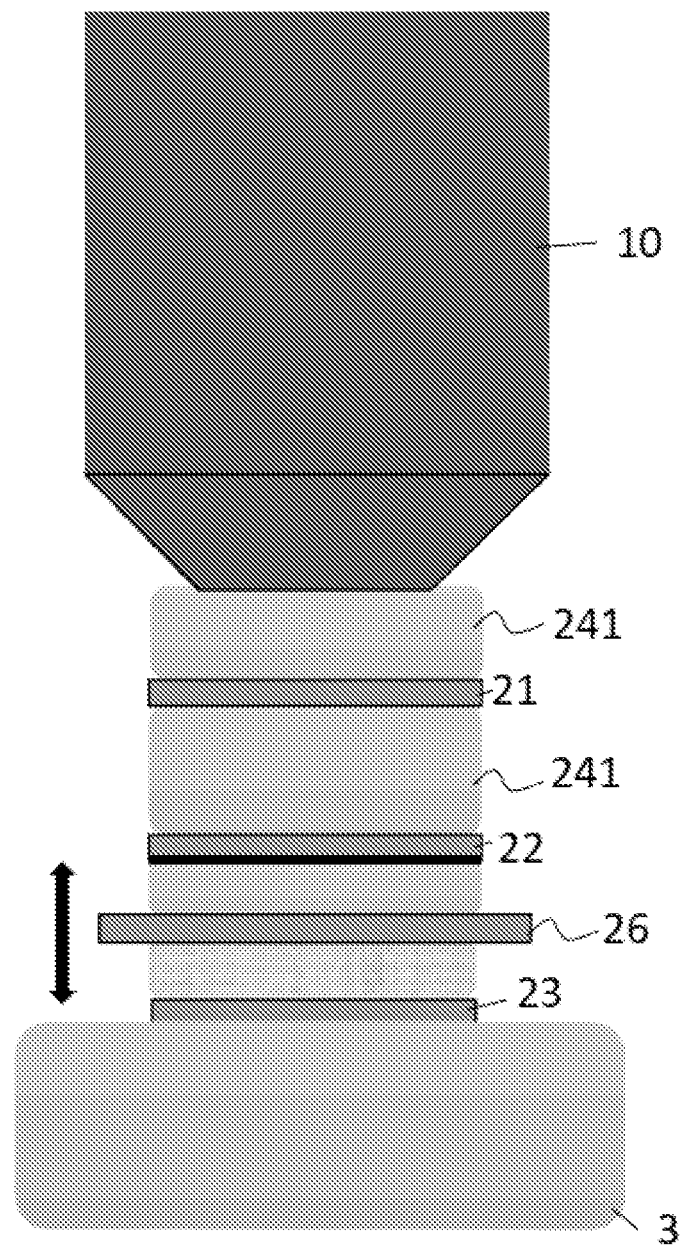
FIG. 8 illustrates an embodiment of an exemplary Mirau type interference module with a refractive adjustment means.

The present invention provides yet another embodiment of a Mirau interference objective module as illustrated in FIG. 8. The exemplary Mirau interference objective module comprises a refractive adjustment means 26 positioned between the beam splitter 22 and the sample plate 23. The first media is filled in spaces inside the Mirau type interference objective module as shown in FIG. 8. In some embodiments, the refractive adjustment means 26 is a glass plate movable in a longitudinal direction, which is the same with the objective's scanning direction.

Figure 9:
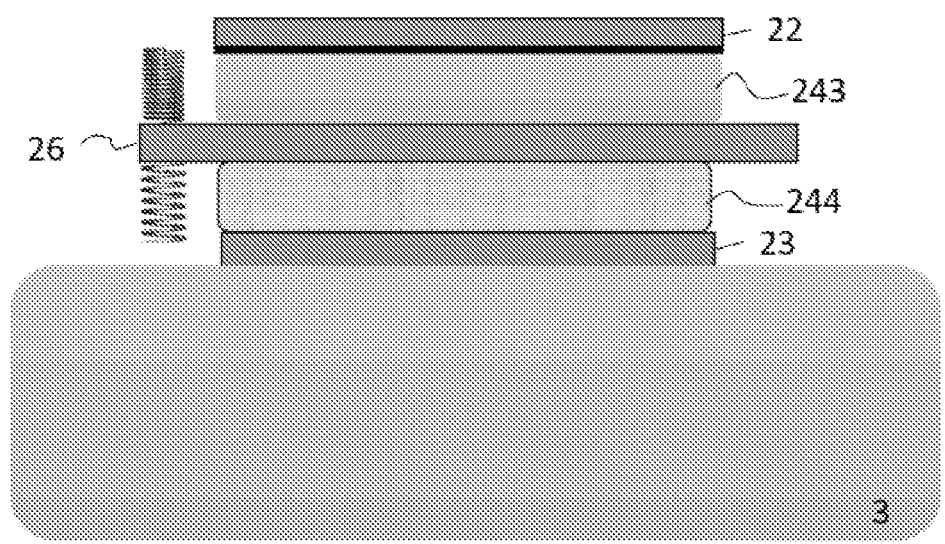
FIG. 9 illustrates an embodiment of an exemplary Mirau type interference module with a refractive adjustment means of FIG. 8 in details.

The present invention also provides an embodiment of the Mirau interference objective module as shown in FIG. 9. The Mirau interference objective module has the same construction as FIG. 8, except a third media 243 is filled in a space between the beam splitter 22 and the refractive adjustment means 26, and a fourth media 244 is filled in a space between the refractive adjustment means 26 and the sample plate 23. In certain embodiments, the refractive index of the third media 243 can be smaller than a refractive index of the fourth media 244. Owing to different refractive index of the third media 243 and the fourth media 244, the interference adjustment means 26 will move asymmetrically during the objective's scanning, so as the average interference of sample arm will be varied in the process of the scanning observation, and the overlapping position of the focal plane and interference plane will be adjusted.

FIG. 10 provides SNR diagrams of an exemplary optical system disclosed herein. FIG. 10A shows the result from a system comprising a Mirau interference objective module as illustrated in FIG. 6 with a glass plate as the refractive adjustment means 25; on the contrary, FIG. 10B shows the result of a system without the glass plate therein. When the refractive adjustment means is inserted between the beam splitter and the sample plate, SNR signal is apparently larger in the depth from 0 to 150 µm (FIG. 10A) than that without the refractive adjustment means (FIG. 10B). However, as the refractive adjustment means is removed, SNR signal will be larger in the depth above 150 µm. Such result can be observed in interference images as shown in FIG. 11A-D. FIGS. 11A and 11B are interference images produced by the optical system corresponded to FIG. 10A, whereas images of FIGS. 11C and 11D are produced by the optical system corresponded to FIG. 10B. When the optical system with a refractive adjustment means inserted between the beam splitter and the sample plate, the images will be clear in shallow depth skin (see arrow) (FIGS. 11A and 11B), which represents the focal plane and the interference plane of the Mirau type interference objective module is overlapped. Instead, the vague signals are shown in deep depth skin (white star) (FIGS. 11C and 11D), which means the focal plane and the interference plane is not overlapped. However, as the refractive adjustment means is removed, the image will be clear in deep depth skin (see arrow) but defocus in shallow depth skin (white star), as shown in FIGS. 11C and 11D. According to this result, the focusing observation depth, also the overlapping position of the focal plane and interference plane, will be effectively varied by the present optical system.

FIG. 12A-C provide interference image resulted from the optical system comprises an interference objective module as illustrated in FIG. 9. Before the scanning measurement started, image signal is strong in shallow sample. (FIG. 12A) When the scanning started, the deep sample images become clear as the refractive adjustment means get close to the sample plate (FIGS. 12B and 12C).

In some embodiments provide An interference objective module comprising an objective, and an interference module comprising a reference plate disposed apart from the objective to provide a reference arm, a beam splitter to split a source light processed from the objective, and a sample plate to translate the split light from the beam splitter to provide a sample arm, wherein the interference module is configured to make a distance of a focal plane and an interference plane of the interference objective module varied during a measurement, and wherein the focal plane and the interference plane of the interference objective module intersect during the measurement. In some embodiments, the interference objective module is immersed in at least two different media with a refractive index similar to the sample. In certain embodiments, the interference objective module comprises a first media, which is filled in a space between the reference plate and the beam splitter; and a second media, which is filled in a space between beam splitter and the sample plate. In certain embodiments, the at least two different media have different refractive indexes. In certain embodiments, the different refractive indexes are in a range of about 1.2 to about 1.8. In some embodiments, the first media comprises water, silicone oil, or glycerol, or the like. In some embodiments, the second media comprises silicone gels, or the like. In some embodiments, the interference objective module is a Mirau type interference objective module, a Michelson type interference objective module, a Linnik type interference objective module, or a Mach Zender type interference objective module.

In some embodiments, the sample plate has a different thickness and/or material from the beam splitter. In certain embodiments, the interference objective module is immersed in one or more media having a refractive index similar to the sample. In certain embodiments, the interference objective module comprises a first media, which is filled in a space between the reference plate and the beam splitter; and a second media, which is filled in a space between beam splitter and the sample plate. In certain embodiments, the first media and the second media have different refractive indexes. In certain embodiments, the different refractive indexes are in a range of about 1.2 to about 1.8. In certain embodiments, the first media comprises water, silicone oil, or glycerol, or the like. In certain embodiments, the second media comprises silicone gels or the like.

In some embodiments, the interference module further comprises a refractive adjustment means positioned between the beam splitter and the sample plate. In certain embodiments, the refractive adjustment means is a glass plate, or a rotational plate, or the like. In certain embodiments, the rotational plate comprises a plurality of portions with different thickness and/or refractive index. In certain embodiments, the refractive adjustment means is a longitudinal movable glass plate. In certain embodiments, the interference module comprises a third media between the beam splitter and the longitudinal movable glass plate, and a fourth media between the longitudinal movable glass plate and the sample plate, wherein a refractive index of the third media is smaller than a refractive index of the fourth media.

In some embodiments provide a device/system comprising: an illumination module configured to provide a source light to an optical interference module, which converts the source light to a line of light and processes light signal; an interference objective module disclosed herein, which handles light from the optical interference module and processes light signal generated from a sample; a two-dimensional camera configured to receive a backscattered interference signal from the sample, and a data processing module which processes the interference signal into an image.

In some embodiments provide a method for imaging a sample by a device/system comprising an invention interference objective module wherein the interference module as disclosed herein is configured to make a distance of a focal plane and an interference plane of the interference objective module varied during a measurement, and making the focal plane and the interference plane of the interference objective module intersect during the measurement.

The invention optical system and interference objective module are useful to adjusting observation depth of a sample in cellular resolution. It is useful in providing information of a sample surface or deep inside of a sample such as skin or cornea. For Mirau type interference optical system, high NA objective will minimize the aberration and optimize the resolution, and the invention interference objective module will effectively improve the observation depth thereof.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What claimed is:

1. An interference objective module comprising
an objective, and
an interference module comprising
a reference plate disposed apart from the objective to provide a reference arm, a beam splitter to split a source light processed from the objective, and
a sample plate to translate the split light from the beam splitter to provide a sample arm, wherein the interference objective module is filled with at least two different media with a refractive index similar to the sample, wherein the interference objective module comprises a first media filled in a space between the reference plate and the beam splitter; and a second media filled in a space between the beam splitter and the sample plate, wherein the first media comprises silicone oils, and the second media comprises silicone gels.

2. The interference objective module of claim 1, wherein the at least two different media have different refractive indexes.

3. The interference objective module of claim 2, wherein the different refractive indexes are in a range of about 1.3 to about 1.5.

4. The interference objective module as claim 1, wherein the sample plate has a different thickness and/or material from the beam splitter.

5. The interference objective module as claim 1, wherein the interference module comprises a refractive adjustment means positioned between the beam splitter and the sample plate.

6. The interference objective module of claim 5, wherein the refractive adjustment means is a glass plate, or a rotational plate.

7. The interference objective module of claim 6, wherein the rotational plate comprises a plurality of portions with different thickness and/or refractive index.

8. The interference objective module as claim 6, wherein the refractive adjustment means is a longitudinal movable glass plate.

9. The interference objective module as claim 8, wherein the interference module comprises a third media between the beam splitter and the longitudinal movable glass plate, and a fourth media between the longitudinal movable glass plate and the sample plate, wherein a refractive index of the third media is smaller than a refractive index of the fourth media.

10. The interference objective module as claim 1, wherein the interference objective module is a Mirau interference objective module, a Michelson interference objective module, a Linnik interference objective module, or a Mach Zender interference objective module.

* * * * *